United States Patent
Duncan et al.

(10) Patent No.: US 7,497,806 B2
(45) Date of Patent: Mar. 3, 2009

(54) EXERCISE APPARATUS FOR A PERSON WITH MUSCULAR DEFICIENCY

(75) Inventors: Michael Robert Duncan, Lane Cove (AU); Simon Geoffrey Parker, Ryde (AU); Branka Curcic, Wakeley (AU)

(73) Assignee: Neopraxis Pty Ltd. (AU)

( * ) Notice: Subject to any disclaimer, the term of this patent is extended or adjusted under 35 U.S.C. 154(b) by 806 days.

(21) Appl. No.: 10/344,636

(22) PCT Filed: Aug. 13, 2001

(86) PCT No.: PCT/AU01/00990

§ 371 (c)(1), (2), (4) Date: Jul. 11, 2003

(87) PCT Pub. No.: WO02/13694

PCT Pub. Date: Feb. 21, 2002

(65) Prior Publication Data

US 2004/0023759 A1 Feb. 5, 2004

(30) Foreign Application Priority Data

Aug. 14, 2000 (AU) .................. PQ9413
Aug. 16, 2000 (AU) .................. PQ9461

(51) Int. Cl.
*A63B 71/00* (2006.01)

(52) U.S. Cl. .................. 482/8; 482/1; 482/9

(58) Field of Classification Search .......... 482/1–9, 482/51, 62, 900–902; 434/247; 602/23; 607/2, 49; 601/23, 27–36

See application file for complete search history.

(56) References Cited

U.S. PATENT DOCUMENTS

| 4,421,336 | A | | 12/1983 | Petrofsky et al. |
| 4,569,352 | A | | 2/1986 | Petrofsky et al. |
| 4,724,842 | A | | 2/1988 | Charters |
| 4,863,157 | A | * | 9/1989 | Mendel et al. ............... 482/62 |
| 5,116,296 | A | | 5/1992 | Watkins et al. |
| 5,284,131 | A | * | 2/1994 | Gray ......................... 601/36 |
| 5,383,911 | A | | 1/1995 | Mann |
| 5,476,441 | A | * | 12/1995 | Durfee et al. ............... 602/23 |
| 5,814,093 | A | * | 9/1998 | Stein .......................... 607/49 |
| 6,872,187 | B1 | * | 3/2005 | Stark et al. .................. 602/16 |

FOREIGN PATENT DOCUMENTS

| EP | 0 219 084 A2 | 4/1987 |
| GB | 2302283 | 1/1997 |
| WO | WO 97/04705 | 2/1997 |
| WO | WO 97/10874 | 3/1997 |

* cited by examiner

*Primary Examiner*—Glenn Richman
(74) *Attorney, Agent, or Firm*—Finnegan Henderson Farabow Garrett & Dunner LLP

(57) ABSTRACT

An exercise system (10) for exercising at least one limb, such as the legs, of a subject with spinal cord injury or deficiency. The system (10) comprises an exercise bicycle (20) having a crank (17) and pedals (16) to which the feet of the subject can be mounted, and a functional electrical stimulation (FES) system (30). The FES system (30) stimulates the muscles of the legs and includes a transducer (51) mountable to at least one of the legs of the subject (12) that outputs signals representative of the position and/or movement of the leg when performing the exercise. The FES system (30) further includes a control means that receives and processes the signals output by the transducer (51) and outputs control signals to a stimulator (35) that through electrodes (53) provides electrical stimulation to the legs of the subject (12) so as to cause the legs to drive the crank (17) of the bicycle (20).

2 Claims, 6 Drawing Sheets

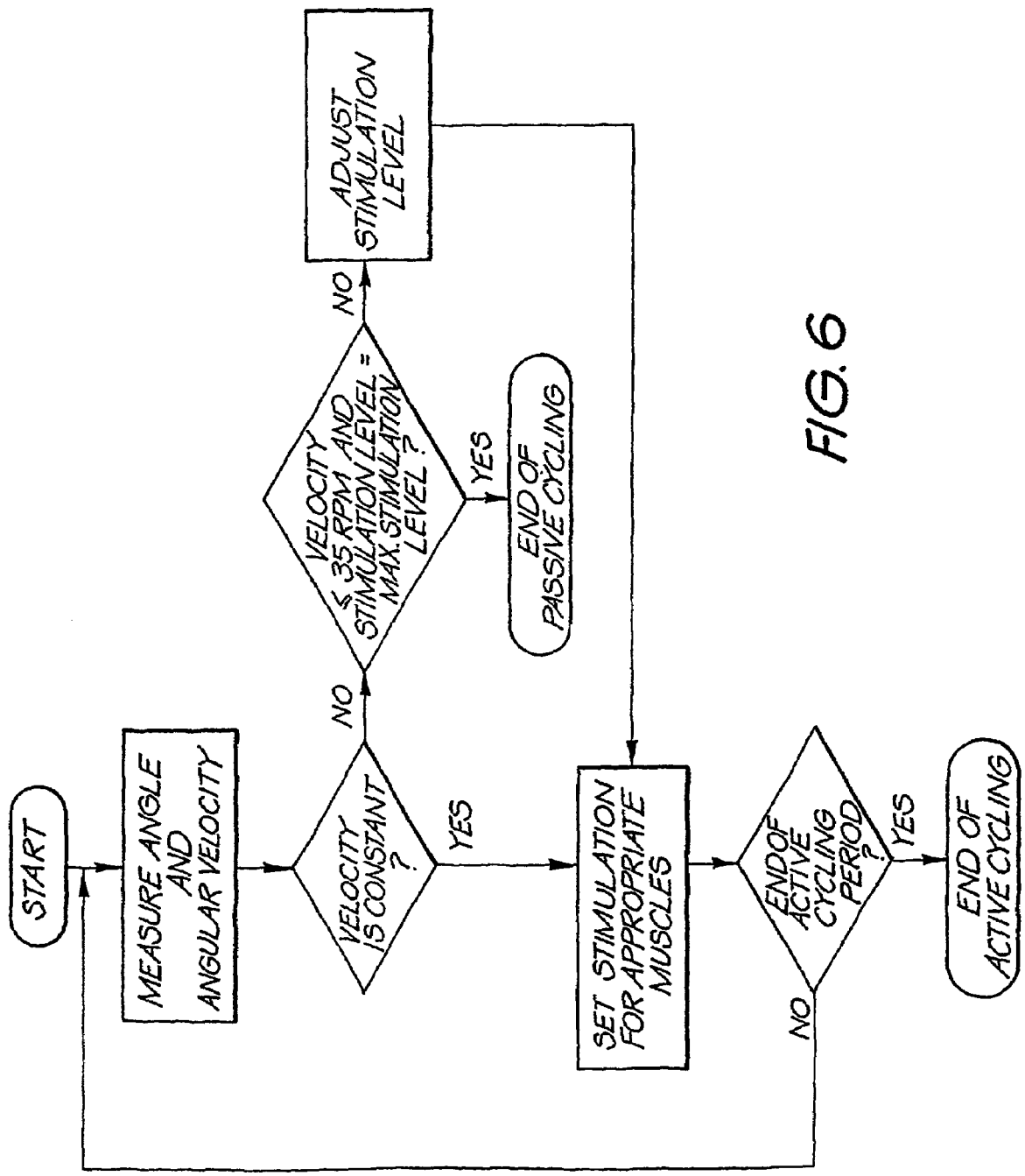

EXERCISE APPARATUS FOR A PERSON WITH MUSCULAR DEFICIENCY

FIELD OF THE INVENTION

The present invention relates to a functional electrical stimulation (FES) system and method of using such a system. More particularly, the invention relates to a device and method for reducing or preventing muscle wastage in persons with spinal cord injury or deficiency.

BACKGROUND OF THE INVENTION

Functional electrical stimulation (FES) systems have been developed using electronic body worn equipment which generates and delivers electrical impulses to the body to control muscle movement Functional electrical stimulation (FES) systems are seen to have particular future application in providing persons suffering from spinal cord injury or deficiency, such as paraplegia, with a capacity to make controlled movements of their dysfunctional limbs.

Functional electrical stimulation systems use electronics to generate electrical impulses. These impulses are then delivered to the nerves or muscles of a subject via electrodes to stimulate movement of the muscles that are otherwise dysfunctional. In order for useful and controlled movements of limbs to be achieved several muscles must usually be operated in concert. This is normally achieved by an algorithm executed under the control of the FES system to deliver a pattern or sequence of stimulation impulses.

In implanted FES systems, the electrical impulses are transmitted from implanted stimulator units via electrically conducting leads to strategically positioned electrodes that deliver the electrical impulses directly to the nerves or muscles. The electrodes are typically positioned remote from the implanted stimulator unit and proximal to the nerves that direct movement of the associated limbs.

A common problem associated with a person losing controlled movement of their limbs is that the muscles that were previously routinely exercised are no longer functional and as such the muscles waste due to lack of exercise. In order to address the problem of muscle wastage, a number of exercise machines have been proposed which provide appropriate exercise to the muscles to prevent muscle wastage. Such machines are, however, typically designed specifically for such use and as a result the machines are generally expensive and cannot easily be adapted for use with alternative FES systems, such as implanted systems as opposed to surface stimulation systems. Also, exercising on a stationary bicycle is a typical critical step in adapting a person to the use of FES systems and as such easy access to such devices is highly desirable Existing exercise bicycles and tricycles for use by paraplegics and the like essentially utilise sensors on the bicycle or tricycle itself, such as on the pedal crank, to initiate muscle stimulation. For example, U.S. Pat. No. 4,421,336 to Petrofsky describes a tricycle having a pedal position sensor mounted on the tricycle that senses the position of the pedal which then leads to the generation of stimulation signals applied to the legs of the subject.

Such systems use a computer to ascertain the position of the pedal and from this position the computer selects the muscles to be stimulated to continue the pedalling motion. The intensity of the stimulus is essentially dictated by the pedalling rate of the subject and the computer detects this rate by measuring the change in pedal position over a fixed unit of time. Unfortunately, such systems are complex and require the exercise bicycle to be dedicated to the specific purpose of providing stimulation to the invalid subject. Existing devices are not easily modified and it is not possible for a common exercise bicycle to be adapted to allow the subject to exercise in the absence of a dedicated machine. Further, existing machines rely upon the input from the bicycle to dictate which muscles are to be stimulated and at what intensity, thereby removing ultimate control of the movement from the subject.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention before the priority date of each claim of this application.

SUMMARY OF THE INVENTION

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The present invention provides a means for exercising the muscles, such as the muscles of the legs, of a subject using function electrical stimulation (FES).

According to a first aspect, the present invention is a functional electrical stimulation system for exercising the limbs of a subject the system comprising:

limb monitoring means having at least one sensor mountable to at least one limb of the subject that outputs signals representative of the position and/or movement of said at least one limb during exercise; and a control means that receives and processes the signals output by the monitoring means and outputs control signals to a stimulating means adapted to provide electrical stimulation to said at least one limb in response to the position and/or movement of said at least one limb detected by the monitoring means;

wherein the control means has a storage means having at least one predetermined action sequence storable therein such that on receipt of signals from the monitoring means, said at least one predetermined action sequence is provided to the stimulating means.

According to a further aspect, the present invention is a functional electrical stimulation system for exercising the legs of a subject by causing the legs to move in a pedalling motion to cause rotation of a rotatable means of an exercise means, the system comprising:

leg monitoring means having at least one sensor mountable to at least one of the legs of the subject that outputs signals representative of the position and/or movement of said at least one leg during the pedaling motion;

a control means that receives and processes the signals output by the monitoring means and, during the exercise, outputs control signals to a stimulating means adapted to provide electrical stimulation to the legs of the subject to cause them to move in the pedalling motion in response to the position and/or movement of said at least one leg detected by the monitoring means.

In the second aspect, the control means can have a storage means having at least one predetermined action sequence storable therein.

In a further embodiment, two or more predetermined action sequences are storable in the storage means and further wherein the system includes a selector means that allows selection of one of the sequences depending on the type of exercise being provided to the limb of the subject. One of the predetermined action sequences can be adapted to stimulate said at least one limb to cause rotation of a rotatable means. In another embodiment, one of the predetermined action sequences can be adapted to stimulate the limb to manipulate an exercise means selected from the group comprising a walking machine, a stepper machine, or a rowing machine. Other suitable exercise devices can be envisaged.

In a preferred embodiment, the rotatable means is a pedal and crank arrangement of an exercise means, such as an exercise bicycle or tricycle. The exercise means can have at least one wheel driven by the rotation of the rotatable means. Alternatively, the crank can bear against a friction plate or brake to provide a degree of resistance to the pedalling motion. The friction plate can be adjustable so as allow the subject or a third party to increase or decrease the degree of friction against the crank.

In one embodiment, the monitoring means can measure the angle of a portion of said at least one limb relative to another portion of this limb. Still further, the monitoring means can measure the angle of a portion of said at least one limb relative to another portion of the subject's body. Yet still further, the monitoring means can measure the angle of a portion of said at least one limb relative to a notional predetermined reference plane. In this embodiment, the reference plane can be a horizontal plane. Other reference planes, including a notional vertical plane can also be envisaged.

In one embodiment, the monitoring means can measure the angle of the thigh and lower leg relative to each other. In a further embodiment, the monitoring means can instead or also measure the angle of the thigh to the torso. In yet another embodiment, the monitoring means can measure the angle of the lower leg to the foot of the subject.

In yet a further embodiment, the monitoring means continuously monitors the changing orientation of the thigh of the subject's leg relative to a notional predetermined reference plane as tie leg rotates the rotatable means. The reference plane can be a horizontal plane. Where the subject is exercising on an exercise bicycle, the monitoring means can continuously measure the changing angles of one of the thighs of the subject as the legs operate the exercise means, such as the pedals of the exercise bicycle.

The at least one sensor can be implantable within said at least one limb of the subject In another embodiment, the sensor can comprise a transducer or inertial sensor. Hereinafter, the sensor will be referred to as a transducer.

The stimulating means or componentry thereof can be implantable within said at least one limb of the subject. In another embodiment, the stimulating means comprises at least one stimulator providing stimulation pulses to one or more electrodes. These one or more electrodes can be implantable within the legs of the subject In another embodiment, the stimulator can be carried by the subject. The stimulator may be carried in or on clothing worn by the subject In another embodiment, the stimulator may be strapped to the subject. Still further, the stimulator can be implanted within the subject When implanted, an external controller can be used to provide control signals and/or power to the implanted stimulator. Radio frequency (RF) communication can be used between the external controller and the implanted stimulator. The implanted stimulator can also provide signals back to the external controller using the RF communication. Electrical leads can extend from the stimulator to-the electrodes. These leads can be totally implantable within the subject or carried externally on the body of the subject. The electrodes can be surface mounted on the skin of the subject, can be percutaneous intramuscular electrodes that are implanted with a minimally invasive needle insertion procedure, or fully implanted electrodes.

In one embodiment, the leg monitoring means can be carried on the subject. The monitoring means can be carried in or on clothing worn by the subject In another embodiment, the monitoring means can be strapped about the limbs, such as the legs, of the subject. In an alternative embodiment, the monitoring means, or componentry thereof, can be implanted within the subject.

In a preferred embodiment, the monitoring means includes at least one transducer that outputs signals representative of the position and/or movement of said at least one transducer and the control means that receives the output signals of said at least one transducer.

Where the monitoring means is measuring the angle of the thigh relative to the lower leg, a transducer can be mounted on both the thigh and lower leg of the subject. Where the measuring means is measuring the angle of the thigh relative to the torso, a transducer can be mounted on the torso and one or both of the legs. More than one transducer on the torso and the legs can also be envisaged. Each of the transducers in this case would output signals to the control means.

The control means can process the output signals of the transducer or transducers and then outputs signals to the stimulating means to provide electrical stimulation to the appropriate muscles within the limbs, such as the legs, of the subject. As described, the control means can store one or more action sequences for application to the subject's muscles which enable exercising of the limbs, such as the pedalling motion. Depending on the position of the limbs as detected by the monitoring means, the control means can execute an algorithm that leads to the provision of electrical stimulation to the appropriate muscle(s) at the appropriate intensity as dictated by the subject or a predetermined programme. The output signals of the transducer or transducers and those of the control means to the stimulating means can comprise electrical or optical signals.

The control means can be adapted to continuously modify the action sequence provided to the stimulating means in response to the signals being received from the transducer or transducers providing information about the position and/or movement of the subjects legs.

In a further embodiment, the at least one predetermined action sequence results in stimulation of the quadriceps, the hamstrings and the gluteal muscles of the subject's legs in order so as to enable a pedalling motion of the leg to cause the rotation of the pedal and crank arrangement.

The control means can include a microprocessor.

In a preferred embodiment, the system can be controlled by the subject. In a further embodiment, the system further comprises an operating means including at least one sensor that monitors the position of a portion of the subject's body other than said at least one monitored limb and outputs predetermined signals in response to detection of predetermined movements by said portion of the subject's body. In this case, detection of a predetermined movement of the torso and/or head of the subject's body can lead to operation of an activation and deactivation means.

In another embodiment, control signals can be provided by the subject adjusting the position or alignment of a hand-held or hand-operated device. In a still further embodiment, control signals can be provided by the subject adjusting controls mounted to the exercise means, such as the exercise bicycle.

Movement of the torso and/or head or operation of controls on the bicycle can be detected by transducers mounted or implanted within these structures. For example, a particular pre-set movement of the torso, for example, can lead to a pre-programmed desired action sequence being provided to the legs so causing the legs to begin or stop a pedalling action on the bicycle. These transducers provide control signals to the control means which in turn instructs the stimulating means to stimulate the desired muscles of the subject.

The activation and deactivation means preferably allows the subject to turn on and off the control means and the FES system when desired. Where the FES system is fully implanted, the activation and deactivation means is preferably controllable from outside the body. In one embodiment, the activation and deactivation means can comprise a switch. Where the control means is implanted, the control means preferably can still be operated through the skin of the subject. The operating means preferably incorporates a locking means to prevent inadvertent activation or deactivation.

The system can include a means of detecting fatigue within the stimulated muscles of the subject.

The FES system can further comprise a power supply, such as a rechargeable battery, that provides power for the system.

According to a further aspect, the present invention is a method of exercising at least one limb of a subject comprising the steps of:

monitoring the position and/or movement of said at least one limb using at least one sensor mounted to the limb and outputting signals representative of said position and/or movement;

processing the signals and selecting an action sequence from one or more predetermined action sequences; and outputting a sequence of stimulation signals to at least said at least one limb.

In one embodiment of this method, the at least one limb is stimulated to cause rotation of a rotatable means of an exercise device, such as the exercise means described above.

In a preferred embodiment, the method relates to exercising one or both legs of a subject.

In a still further aspect, the present invention is a method of exercising at least one limb of a subject comprising the steps of:

mounting said at least one limb to an operable member of an exercise means;

externally driving the operable member and so causing an exercising movement of said at least one limb;

monitoring the position and/or movement of said at least one limb using at least one sensor mounted to the limb and outputting signals representative of said position and/or movement;

processing the signals and providing electrical stimulation to at least said at least one limb so as to cause said at least one limb to drive the operable member; and discontinuing external driving of the operable member.

In this aspect, the step of externally driving the operable member can occur for a predetermined time period. The electrical stimulation can comprise a sequence of stimulation impulses. The sequence can be selected from one or more predetermined action sequences.

In this aspect, the step of discontinuing external driving of the operable member can occur after the step of outputting stimulation signals to said at least one limb. In another embodiment, the step of discontinuing external driving can occur simultaneously with commencement of outputting stimulation signals or prior to this step.

In this aspect, the step of providing stimulation signals to said at least one limb so as to cause said at least one limb to drive the operable member preferably occurs for a predetermined period of time.

In this aspect, following commencement of the step of providing the electrical stimulation, the intensity of the stimulation can gradually increase to a predetermined maximum. Prior to the end of the predetermined period of time of providing the electrical stimulation, the intensity of the stimulation can gradually decrease.

According to a still further aspect, the present invention is an exercise system for exercising at least one limb of a subject with spinal cord injury or deficiency, the system comprising:

an exercise means comprising a movable operable member drivable by a driving means, said at least one limb being mountable to the operable member; and a functional electrical stimulation (FES) means for stimulating the muscles of said at least one limb, the FES means comprising limb monitoring means having at least one sensor mountable to said at least one limb that outputs signals representative of the position and/or movement of said at least one limb and a control means that receives and processes the signals output by the monitoring means and outputs control signals to a stimulating means adapted to provide electrical stimulation to said at least one limb of the subject so as to cause said limb to drive the operable member.

In the preceding two aspects, the operable member can comprise a pedal and crank arrangement of an exercise means. The rotatable pedal and crank arrangement can drive at least one wheel. Alternatively, a friction plate or brake can bear against the crank and provide a degree of resistance to the pedalling motion. The friction plate is preferably adjustable. The limb being exercised can be one or both legs of the subject. The at least one sensor can monitor the position and/or movement of one or both legs of the subject.

In one embodiment, the electrical stimulation can be output to both legs of the subject.

The driving means of the exercise means can be used to drive the pedal and crank arrangement of the exercise means for at least the predetermined time period. The predetermined time period can range between about 15 seconds and about 20 minutes, more preferably between about 1 minute and about 10 minutes, still more preferably between about 1 minute and about 5 minutes, and yet still more preferably between about 2 and about 3 minutes.

In one embodiment, the driving means can be operable by the subject. The driving means can comprise a hand crank. The hand crank can be controlled by the subject or a third party. In another embodiment, the driving means can comprise a motor, such as an electric motor, that drives the operable member.

In a preferred embodiment, the control means further detects and monitors the movement of the operable member when driven by the driving means and activates the stimulating means following the predetermined time period.

The control means on activating the stimulating means can gradually increases the intensity of the electrical stimulation to a predetermined maximum.

The FES means and the exercise means can have the features of the equivalent systems also defined herein.

The present invention provides a system and method that directly measures the position and/or movement of one or more limbs, such as a leg, of a person with spinal cord deficiency operating an exercise means, such as an exercise bicycle. The system then outputs stimulation signals to move the legs in a manner suitable to operate the exercise means, such as drive the pedals of the bicycle. The system and method provides a relatively inexpensive means for the subject to exercise their otherwise dysfunctional muscles as the system can be used on any form of bicycle, or one that has undergone relatively minor modification, and also provides the subject with experience in use of a FES system.

BRIEF DESCRIPTION OF THE DRAWINGS

By way of example only, preferred embodiments of the invention are now described with reference to the accompanying drawings, in which:

FIG. 6 is a flow chart depicting the steps undertaken by the operating system of the exercise system when the subject is engaged in active cycling on the exercise system.

PREFERRED MODE OF CARRYING OUT THE INVENTION

Figure 1:
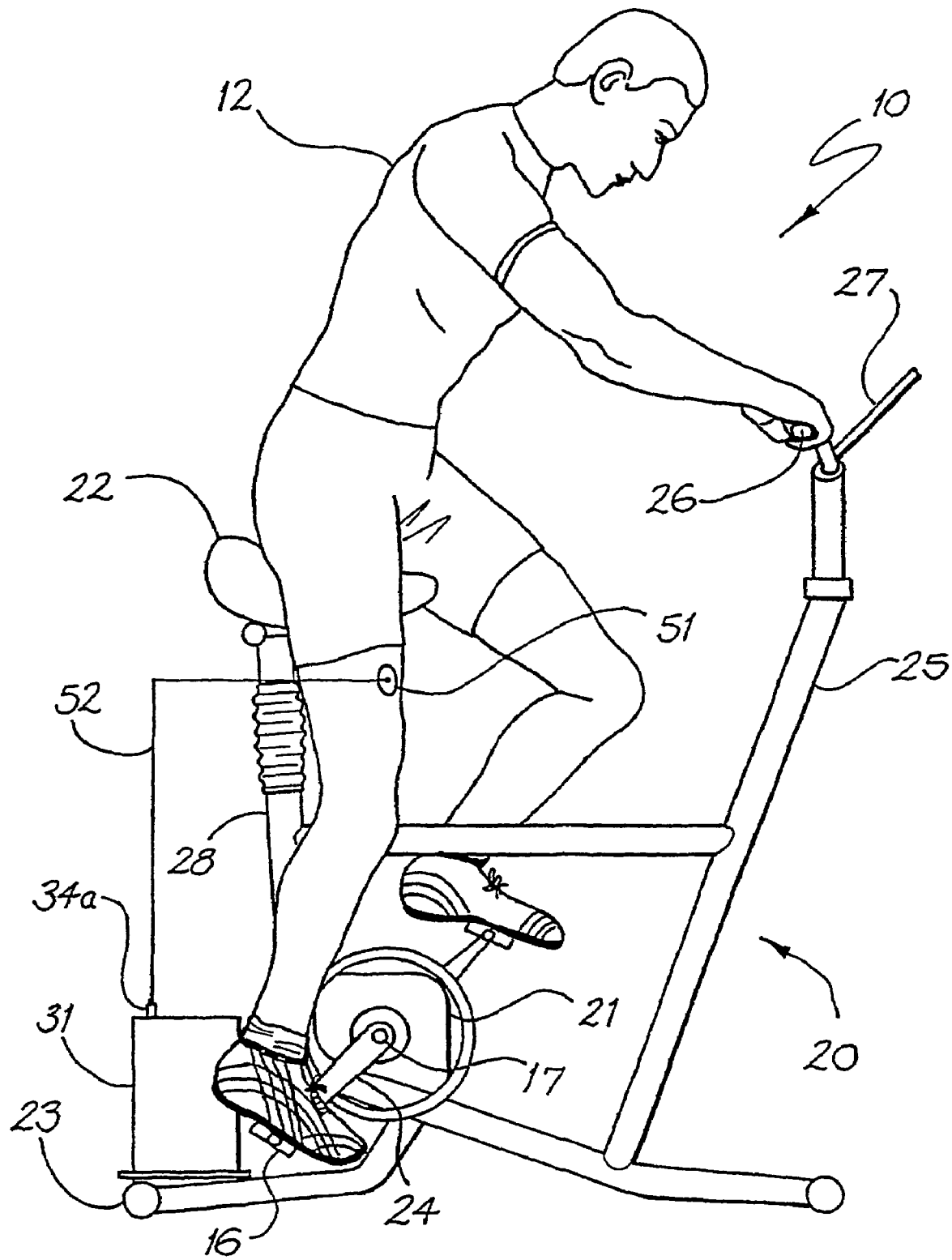
FIG. 1 is a side elevation view of one embodiment of an exercise system comprising both a functional electrical stimulation (FES) system and an exercise bicycle according to the present invention.

An exercise apparatus for use by a person suffering from spinal cord injury or deficiency is depicted generally as 10 in the drawings.

In the depicted embodiment, the apparatus 10 includes a stationary exercise bicycle 20 of a generic type. As used herein, the term bicycle is to be understood as encompassing stationary devices adapted to replicate the pedalling motion of a standard street or track bicycle. It will be appreciated that such exercise devices while known in the art as "exercise bicycles" do not normally have two wheels. Indeed, the exercise bicycle as depicted in FIG. 1, while having a rotatable crank 17 and pedals 16 does not have any wheels. Rather, the crank 17 extends into a drive box 21. Within the drive box, an adjustable friction plate bears against the crank 17 and provides a degree of friction against movement of the crank 17. It will be understood that the exercise bicycle can comprise any exercise bicycle known in the art.

The exercise bicycle 20 has a saddle-shaped seat 22 to allow the person 12 using the apparatus to be supported on the bicycle 20. Given that the present invention is adapted for use by a person suffering spinal cord injury or deficiency, it will be appreciated that the seat 22 may have a belt or other means to assist in restraining the person 12 on the seat 22. In FIG. 1, a belt is not depicted for reasons of clarity.

The exercise bicycle 20 has a base 23 adapted to rest on a flat surface, such as a floor. Extending upwardly from the base 23 is the drive box 21. The crank 17 extends through the box 21 and is terminated at each end with respective crank arms 24 that support the respective pedals 16. Extending upwardly from the base 23 and forwardly from the drive box 21 is a support member 25 for a set of handlebars 26. The handlebars 26 can be gripped by the hands of the person 12 and assists them in maintaining their position on the bicycle 20. The handlebars can have a display screen 27 extending upwardly therefrom. The depicted screen 27 provides a means for the person 12 to operate the apparatus 10, through the use of touchpads on the screen 27. The touchpads provide the person 12 with one means of activating or deactivating the apparatus 10. The display screen 27 is also used to provide feedback to the person 12 on their exercise, such as time elapsed in undertaking the exercise.

The seat 22 is supported on the base by a further support member 28 extending upwardly from the base 23 rearwardly of the drive box 21. The seat 22 is adjustable in height relative to the pedals 16 to allow the apparatus 10 to be used by persons having a range of body shapes and sizes.

Mounted on the base 23 rearwardly of the seat support member 28 is a housing 31 of a functional electrical system 30. The housing 31 is used to protect the componentry of the functional electrical system 30. The housing 31 is not depicted to scale in FIGS. 1 and 2. While depicted in this position on the system 10, the housing 31 could be mounted on another location on the exercise bicycle 20. Still further, the housing 31 could be carried on the person 12, such as in the person's clothing or in a backpack carried by the person 12. Yet still further, some of the componentry within the housing 31 can be implanted within the person 12.

Figure 3:
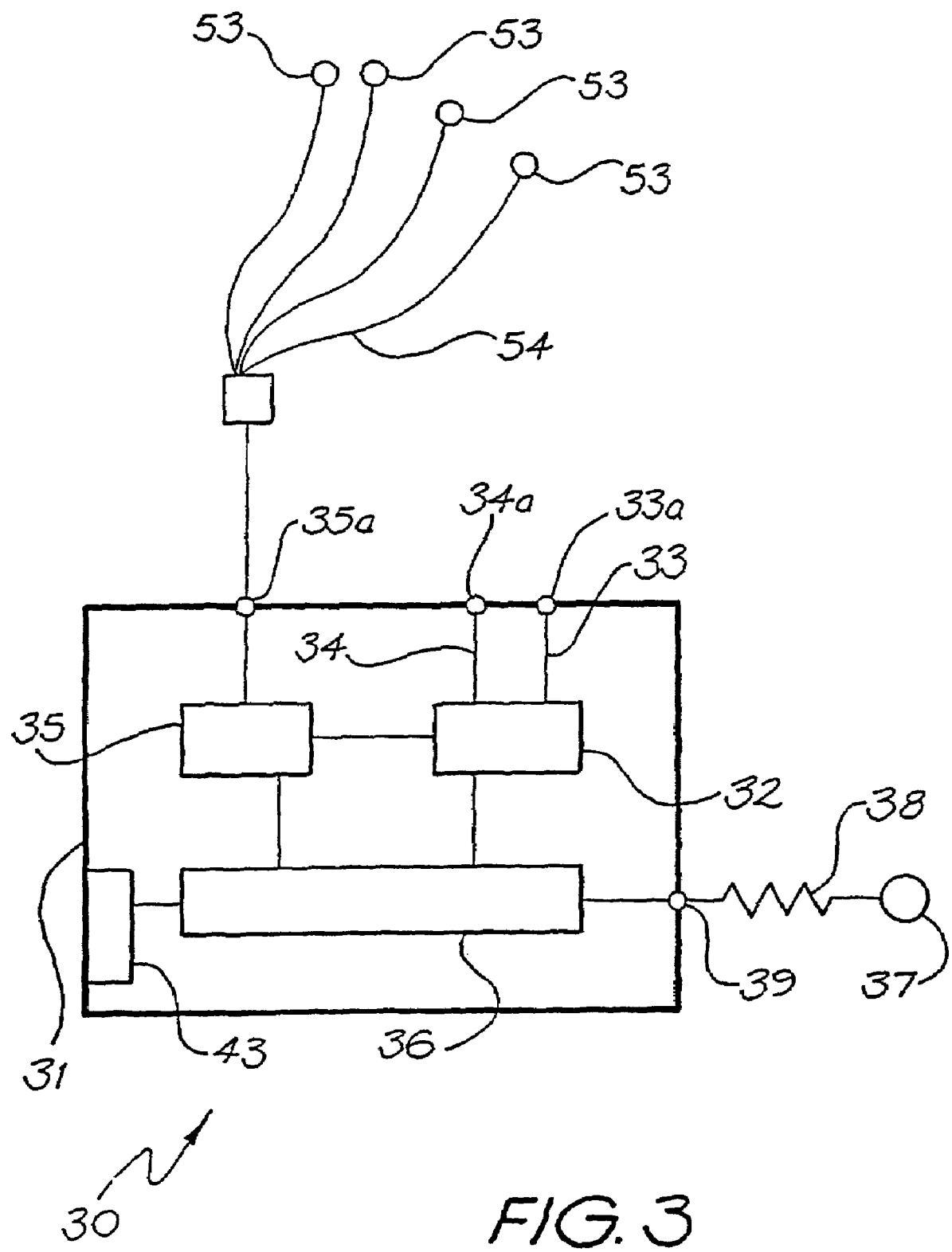
FIG. 3 is a block diagram of one embodiment of the functional electrical simulation system according to the present invention.

In the embodiment depicted in FIG. 3, the housing 31 houses a control means 32. The control means 32 receives a first set of signals through a first signal path 33 provided by a cable (not depicted) extending from the display screen 27 to an electrical connector 33a on the housing 31. The signals provided through signal path 33 typically represent basic control signals from the person 12. For example, the person 12 through signal path 33 can turn the system 30 on and off and can control the rate of muscle stimulation output by the stimulator 35 and so control the rate of pedalling of the pedals 16.

The control means 32 also receives a second set of output signals through a second signal path 34 provided by a cable 52 extending from a transducer 51 mounted to the thigh of one of the legs of the person 12 to a connector 34a on the housing 31. The cable 52 is shown schematically in FIG. 1 and can be envisaged, in one embodiment, as being a flexible cable extending between the transducer 51 and the connector 34a.

The control means 32 is pre-programmed to receive the signals fed by signal paths 33 and 34 and then output a pre-determined sequence of signals to the stimulator 35 in response to the detected position of the crank 17 as determined from the transducer 51 mounted to the right leg. In this way, the control means 32 is able to output a stimulation pattern that sets the legs moving in a cycling pattern and so pedalling the pedals 16 of the exercise bicycle 20. For example, the action sequence can comprise a sequence of stimulations provided in order to the quadriceps, hamstrings and the gluteal muscles of the subject's respective legs so as to cause the legs to move the pedals 16 in a cycling action. In this regard, it will be appreciated that the action sequence to one leg will be 180° out of phase to the action sequence provided to the person's other leg.

While in the depicted embodiment, a single transducer is shown mounted to the thigh of one of the legs of the person 12, it will be appreciated that more than one transducer or inertial sensor could be mounted on the person 12 in other positions. For example, each leg could have a transducer mounted thereto. Still further, one or more transducers could be mounted to the torso and/or head of the person 12.

The control means 32 can comprise a microprocessor and include a data storage device that stores measured leg movement resulting from electrical stimulations. The control means 32 also includes a comparator that can compare the various stored measured leg movements. If the comparator detects a change in leg movement, this is, in the depicted embodiment, interpreted by the control means 32 as resulting from muscle fatigue within that limb.

Figure 4:
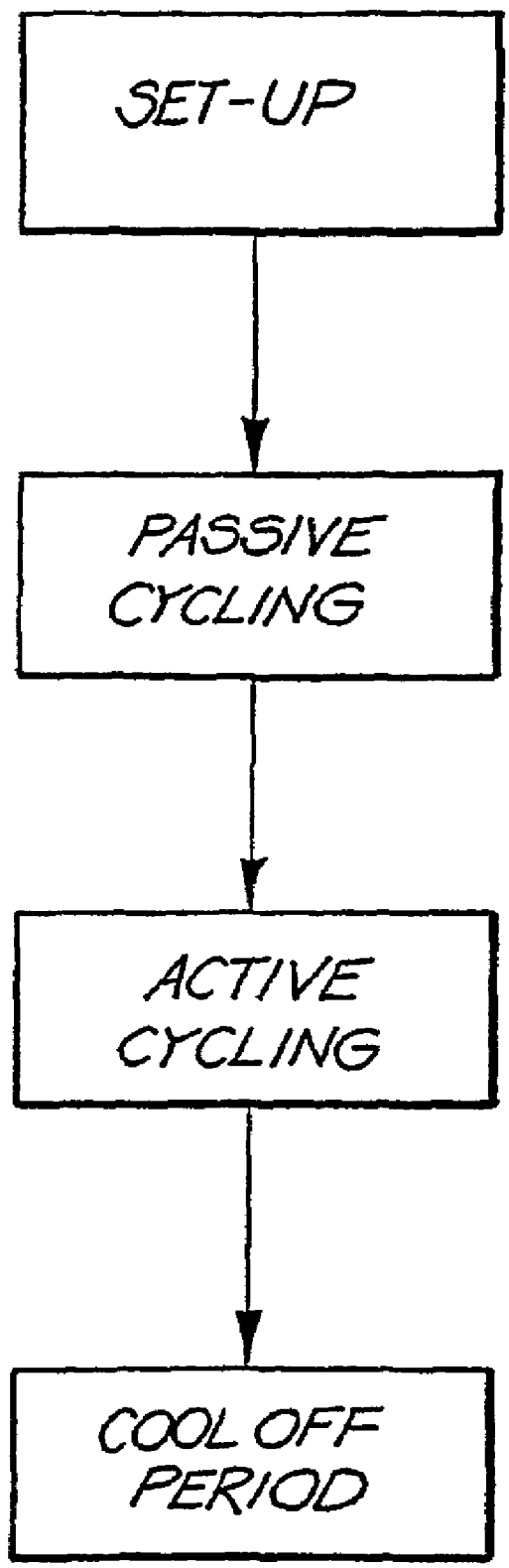
FIG. 4 is a flow chart depicting the states of operation of the exercise system according to the present invention.

A typical exercise strategy for a person 12 using the system 10 is depicted in FIG. 4. During Set-Up, the person 12 will need to set up the functional electrical system 30 such that it is adapted to output a suitable action sequence for use with an exercise bicycle. In this regard, the control means 32 can have a number of suitable pre-determined action sequences stored therein ready for selection by the person 12 for use when required. For example, the person 12 can input to the functional electrical stimulation system 31 an intention to perform an exercise routine or use the touchpads on the display screen 27 to inform the system 30 that a cycling action of the legs is required and that accordingly a suitable action sequence from the stimulator will be required. The system 30 on receiving information as to the type of exercise to be performed by the person 12 can then select the appropriate action sequence from those sequences already stored in the control means 32. Where another exercise is to be undertaken by the person 12, such as walking on a treadmill of a walking machine or performing a rowing action on a rowing machine, the control means 32 can select a different action sequence suitable to ensure the legs of the person 12 move in a walking motion on the treadmill or in a rowing action on the rowing machine.

Also during Set-Up, the person will connect the transducer 51 to their right thigh and mount the seat 22 of the bicycle 20. An appropriate number of stimulating electrodes 53 are also mounted to the legs of the person 12. The electrodes 53 are depicted in FIG. 3 and are not depicted in FIG. 1 for reasons of drawing clarity. The electrodes 53 receive stimulation pulses via cables 54 connected to the stimulator 35 by the connector 35a in the housing 31. More or less electrodes than that depicted in FIG. 3 can be envisaged depending on the requirements of the device. The cables 54 depicted in FIG. 3 are also not necessarily to scale. More than one electrode per cable 54 may also be envisaged as being encompassed within this description. While the depicted arrangement relies on use of external electrodes, it should be appreciated that electrodes could be implanted within the person 12 with stimulation pulses being provided from a stimulator also implanted within the body of the person 12. Such an implanted stimulator could be used in association with an external device that communicates with the stimulator and receives control signals from the control means 32. For example, radio frequency (RF) transmission could be used to deliver signals from the external device to the implanted stimulator.

Once the person is mounted on the seat 22 with their feet on the pedals 16 and all appropriate electrical connections have been made, the system 10 can move into a Passive Cycling state. While in this state, the crank arms 24 are moved by an external drive means to rotate crank 17. In this state, the drive means needs to be something other than the person's legs.

The drive means can merely be the user themselves manually pushing on their legs to cause pedaling motion or may comprise an electric motor housed within the drive box 21. In another embodiment, a third person can simply turn the crank 17 for the person 12.

Figure 2:
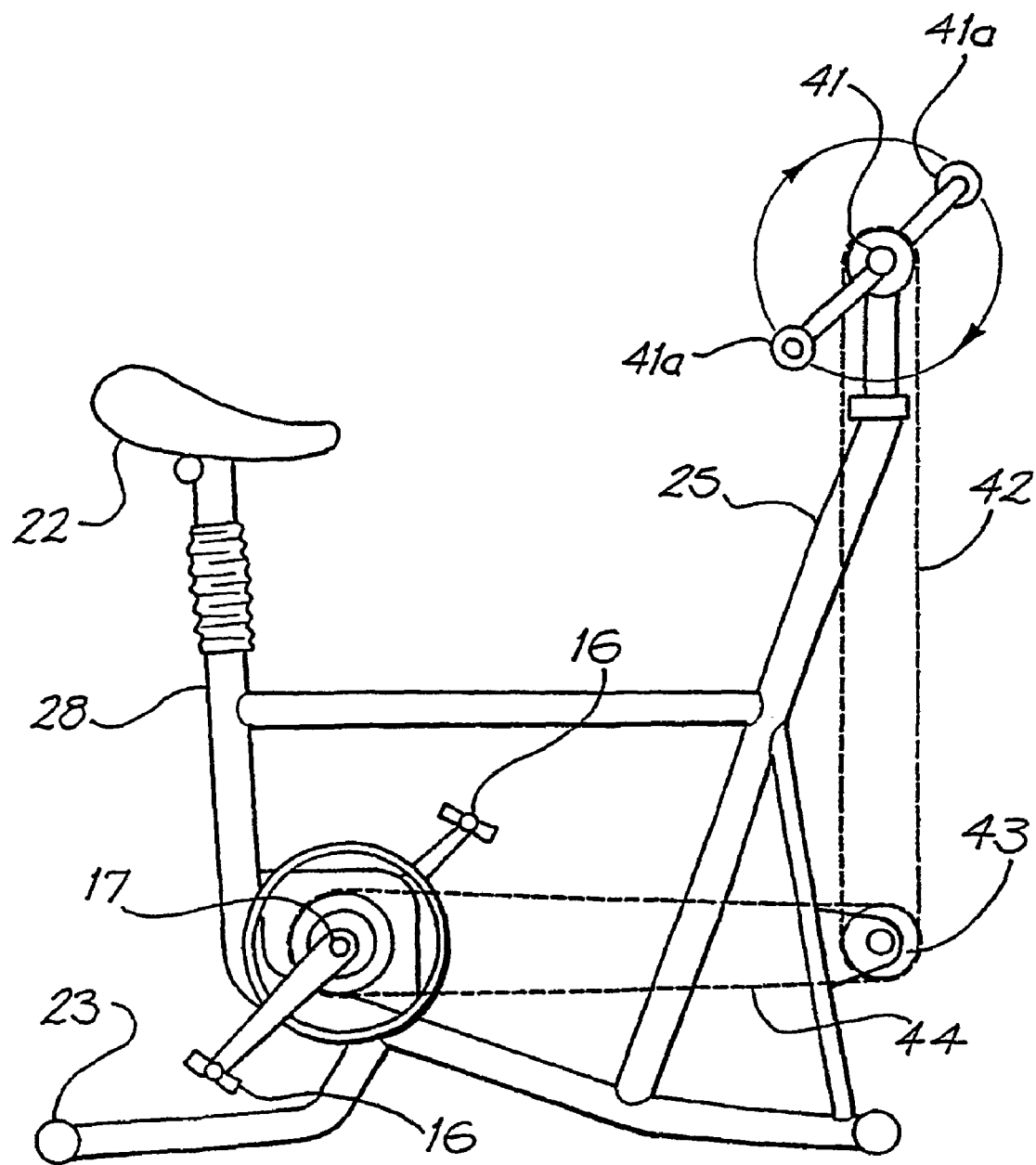
FIG. 2 is a side elevation view of a modified version of the exercise system depicted in FIG. 1.

In a still further arrangement, and as is depicted in FIG. 2, the person (not depicted in FIG. 2) can use their hands to turn a hand crank 41 mounted on support member 25. The hand crank 41 has hand grips 41a and drives a chain 42 that extends to a drive wheel 43 mounted forwardly of the support member 25. A still further chain 44 extends from the drive wheel 43 to the crank 17. By turning the hand crank 41, the crank 17 turns through the action of the respective chains 42,44 and the drive wheel 43. This allows the person 12 to commence a pedalling action of their legs, despite having a leg muscle deficiency.

The Passive Cycling state is desirable as it assists in reducing spasms within the legs following commencement of the exercise. The passive cycling state also allows the pedaling motion of the individual to be calibrated for the specific device and the various angles of the limbs to be determined to take into consideration different exercise bicycles and the like. The Passive Cycling state can last from about 2-3 minutes, however, longer or shorter time periods can be envisaged.

While in the Passive Cycling state, the pedalling motion of the legs can be monitored using the transducer 51 on the right thigh. After a period of passive cycling, such as about 2 minutes, the control means 32 can commence to output an action sequence to the stimulator 35 which in turn provides stimulation pulses to the respective electrodes 53 mounted on the person 12. In the depicted arrangement, the intensity of stimulation is at first relatively low and then gradually increases.

Where the person 12 is using the hand crank 41 to turn their legs or is manually causing the pedalling motion, the person 12 can disengage the hand crank 41 or the manual action once the intensity of stimulation has reached a level sufficient to result in turning of the crank 17 simply by the electrical stimulation being provided to the legs. If an electric motor is used, the control means 32 can be arranged to disconnect the motor or turn it off once an appropriate level of stimulation is being provided to the legs and/or the signals output by the transducer 51 indicate a cycling motion is occurring.

Figure 5:
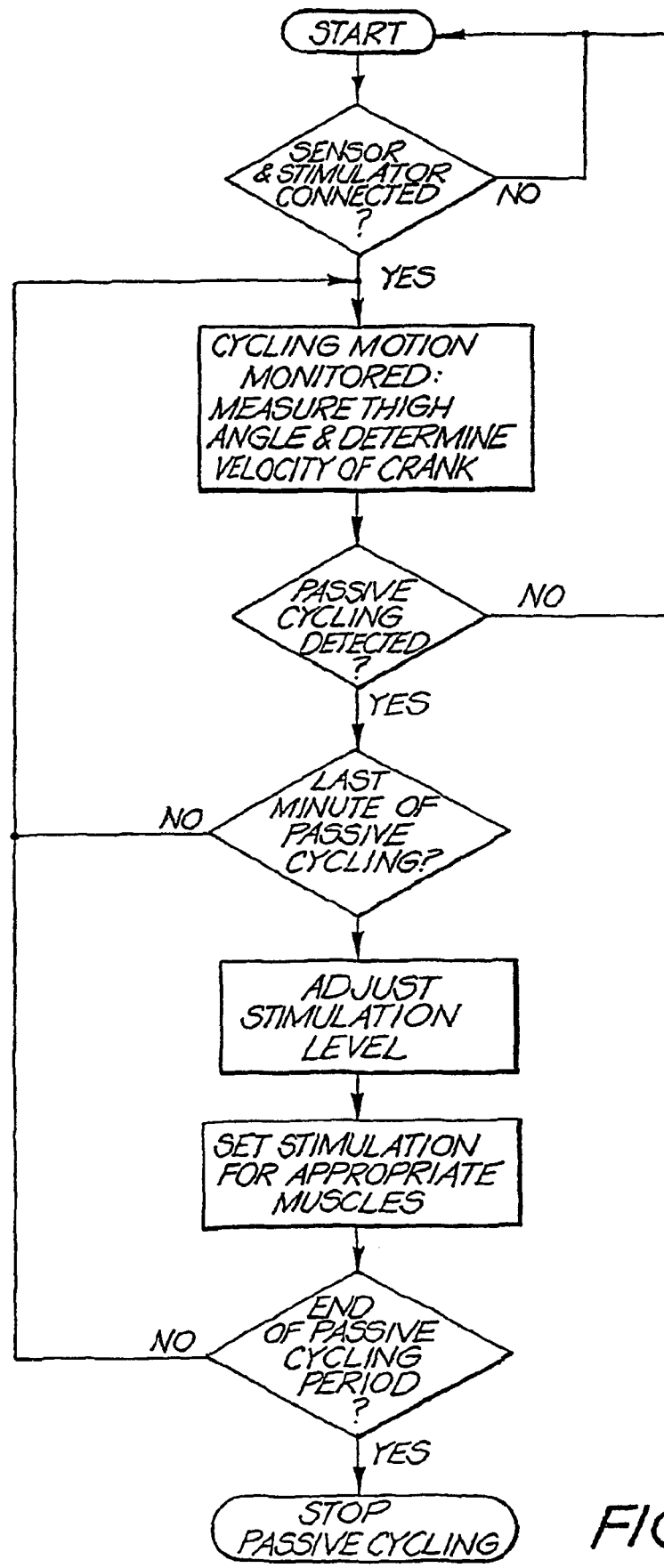
FIG. 5 is a flow chart depicting the steps undertaken by the operating system of the exercise system when the subject is engaged in passive cycling on the exercise system.

A flowchart depicting the process steps of the control means 32 leading up to the end of the Passive Cycling state is provided in FIG. 5. Once the transducer 51 and stimulator 35 are operational, the control means 32 monitors the output of the transducer 51 on the right thigh to determine if passive cycling has been detected. Once detected, the control means measures the time of passive cycling. If a maximum period of 3 minutes is envisaged, the control means 32 on detecting that two minutes has expired begins to increase the intensity of the stimulation output by the stimulator 35 to the electrodes 53. This can continue until a predetermined maximum level of stimulation is being provided to the muscles of the legs of the person 12. Once the Passive Cycling state has ended (eg. 3 minutes have elapsed), the control means 32 fully controls the cycling motion of the legs through the provision of stimulation to the legs.

During the Active Cycling state, the cycling movement of the legs is fully controlled by the control means 32 outputting functional electrical stimulation to the person's legs. The exercise can occur for a predetermined period of time and then the control means 32 can automatically discontinue provision of stimulation. The person 12 can also stop the exercise of the legs when required simply by depressing an appropriate touchpad on the display screen 27 or the functional electrical stimulation system 31, which sends a deactivation signal to the control means 32 through signal path 33.

FIG. 6 depicts a flowchart of the operation of the control means 32 during the Active Cycling state. While in this state, the control means 32 continuously monitors the output of the transducer 51 and from this determines the crank angle of the crank 17 and its angular velocity. Once the velocity is determined to be constant, the control means 32 controls the provision of stimulation until such time as the predetermined period of active cycling has elapsed or a signal is received indicative that the person 12 wishes to discontinue active cycling. If the angular velocity is not constant, the angular velocity is monitored through use of the transducer. In the depicted flowchart, if the angular velocity is less than or equal to 35 rpm at maximum stimulation level, then stimulation is immediately stopped and active cycling comes to an end. If not, the stimulation level is adjusted.

As depicted, the system 30 can have a Cool Off Period during which stimulation levels output by the stimulator are gradually reduced by the control means 32. This gradual reduction down to zero stimulation can occur over a period of seconds, minutes or longer.

The transducer 51 mounted to the thigh of the person 12 provides a signal output representative of the angle of the thigh relative to a notional horizontal plane. From a determination of this angle, the crank angle of the crank 17 can be determined. In the arrangement depicted in FIG. 1, the transducer is mounted to the right thigh of the person 12. The position of the left leg of the person 12 is assumed for the purposes of this analysis in this embodiment to be 180° out of phase relative to the right leg.

In monitoring the cycling motion of the legs of the person 12, 0° is taken to correspond to the right thigh position when the right pedal of the exercise bicycle 20 is at its top most position. The transducer 51 will during a full revolution of the crank 17 move through an arc of $(2\theta)°$, where $\theta$ is the angle that the transducer moves through between the top most and bottom most position of the pedals 16.

As the transducer moves during one revolution of the crank 17, the same angles will be detected twice. The angles belonging to the first half of the revolution can be distinguished from those belonging to the second half of the revolution based upon the angle derivative, ie whether the angle is increasing or decreasing. Based on the determined minimum and maximum angles measured by the transducer 51, a converter value can be calculated by the control means 32 which is used to convert measured transducer angles into a corresponding crank angle. The measured angle range will depend on the body position of the person 12. Although the person 12 may be fixed in position, small changes in the minimum and maximum angles detected by the transducer can result in relatively big changes in the measured crank angle. As such, the angle range measured by the transducer will be constantly monitored and the converter value updated to account for such movement.

The transducer 51 mounted to the leg also provides a signal output representative of the movement of the legs following electrical stimulation by the stimulator 35. For example, the transducer can inform the control means 32 that the stimulator 35 has or has not achieved the outcome for the legs expected by the provided stimulation.

As depicted in FIG. 3, the system 30 further comprises an operating means 36 that receives signals from a transducer 37 adapted to monitor the position of a portion of the subjects body other than the monitored limb. The transducer 37 outputs signals through cable 38 connected to connector 39 in the housing 31. The transducer 37 and cable 38 are not depicted to scale in FIG. 3. More than one such transducer 37 can also be envisaged. On receipt of a predetermined signal from the transducer 37, the operating means can activate or deactivate the control means 32 and/or the stimulator 35. For example, the transducer 37 can be mounted to the head of the person 12, and adapted to output a predetermined signal on determination of a particular movement of the person's head relative to the their torso. This provides the person 12 with a ready means to activate or deactivate the FES system simply by a predetermined movement of their head.

The present system 10 provides a means of allowing a person 12 to exercise their otherwise dysfunctional muscles using an exercise bicycle. This serves to reduce or prevent wastage of those muscles as well as serve as a means of introducing a person to functional electrical systems.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A functional electrical stimulation system for exercising the limbs of a subject that are at least partially paralyzed, the system comprising:

a limb monitor having at least one sensor mountable to at least one of the at least partially paralyzed limbs of the subject that outputs signals representative of the position or movement of said at least one limb during exercise; and a controller that receives and processes the signals output by the monitor and outputs control signals to a stimulator adapted to provide electrical stimulation to said at least one limb in response to the position or movement of said at least one limb detected by the monitor;

wherein the controller has a storage unit having at least one predetermined action sequence storable therein such that on receipt of signals from the monitor, said at least one predetermined action sequence is provided to the stimulator;

wherein the system further comprises an operator including at least one sensor that monitors the position of a portion of the subject's body other than said at least one monitored limb and outputs predetermined signals in response to detection of predetermined movements by said portion of the subject's body;

wherein detection of a predetermined movement of the torso of the subject's body leads to activation or deactivation of the system.

2. A functional electrical stimulation system for exercising the legs of a subject that are at least partially paralyzed by causing the legs to move in a pedaling motion to cause rotation of a rotator of an exerciser, the system comprising:

a leg monitor having at least one sensor mountable to at least one of the at least partially paralyzed legs of the subject that outputs signals representative of the position or movement of said at least one leg during the pedaling motion;

a controller that receives and processes the signals output by the monitor and, during the exercise, outputs control signals to a stimulator adapted to provide electrical stimulation to the legs of the subject to cause them to move in the pedaling motion in response to the position and/or movement of said at least one leg detected by the monitor;

wherein the system further comprises an operator including at least one sensor that monitors the position of a portion of the subject's body other than said at least one monitored leg and outputs predetermined signals in response to detection of predetermined movements by said portion of the subject's body;

wherein detection of a predetermined movement of the torso of the subject's body leads to activation or deactivation of the system.

* * * * *